(12) United States Patent
Kwon

(10) Patent No.: US 6,482,604 B2
(45) Date of Patent: *Nov. 19, 2002

(54) NON-OR MINIMALLY INVASIVE MONITORING METHODS USING PARTICLE DELIVERY METHODS

(75) Inventor: Sung Yun Kwon, Fremont, CA (US)

(73) Assignee: PowderJect Research Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/803,828

(22) Filed: Mar. 12, 2001

(65) Prior Publication Data

US 2001/0029957 A1 Oct. 18, 2001

Related U.S. Application Data

(63) Continuation of application No. 09/390,068, filed on Sep. 3, 1999, now Pat. No. 6,207,400.
(60) Provisional application No. 60/099,157, filed on Sep. 4, 1998.

(51) Int. Cl.$^7$ .............. C12Q 1/54; C12Q 1/00; C12Q 1/26
(52) U.S. Cl. .......... 435/14; 435/4; 435/283.1; 435/25
(58) Field of Search .......... 435/14, 4, 283.1, 435/25

(56) References Cited

U.S. PATENT DOCUMENTS

| | | | |
|---|---|---|---|
| 4,344,438 A | 8/1982 | Schultz | 128/634 |
| 4,401,122 A | 8/1983 | Clark, Jr. | 128/635 |
| 4,945,050 A | 7/1990 | Sanford et al. | 435/172.1 |
| 5,036,861 A | 8/1991 | Sembrowich et al. | 128/763 |
| 5,076,273 A | 12/1991 | Schoendorfer et al. | 128/632 |
| 5,101,814 A | 4/1992 | Palti | 128/635 |
| 5,139,023 A | 8/1992 | Stanley et al. | 128/637 |
| 5,140,985 A | 8/1992 | Schroeder et al. | 128/632 |
| 5,149,655 A | 9/1992 | McCabe | 435/287 |
| 5,204,253 A | 4/1993 | Sanford | 435/172.3 |
| 5,279,543 A | 1/1994 | Glickfeld et al. | 604/20 |
| 5,342,789 A | 8/1994 | Chick et al. | 436/501 |
| 5,362,307 A | 11/1994 | Guy et al. | 604/20 |
| 5,445,611 A | 8/1995 | Eppstein et al. | 604/49 |
| 5,458,140 A | 10/1995 | Eppstein et al. | 128/632 |
| 5,628,310 A | 5/1997 | Rao et al. | 128/633 |
| 5,636,632 A | 6/1997 | Bommannan et al. | 128/632 |
| 5,722,397 A | 3/1998 | Eppstein | 128/633 |
| 5,730,714 A | 3/1998 | Guy et al. | 604/20 |
| 5,735,273 A | 4/1998 | Kurnik et al. | 128/635 |
| 5,771,890 A | 6/1998 | Tamada | 128/635 |
| 5,827,183 A | 10/1998 | Kurnik et al. | 600/345 |
| 5,885,211 A | 3/1999 | Eppstein et al. | 600/309 |
| 5,902,603 A | 5/1999 | Chen et al. | 424/449 |
| 5,954,685 A | 9/1999 | Tierney | 604/20 |
| 6,022,316 A | 2/2000 | Eppstein et al. | 600/309 |
| 6,030,399 A | 2/2000 | Ignotz et al. | 606/167 |
| 6,040,194 A | 3/2000 | Chick et al. | 436/501 |
| 6,091,975 A | 7/2000 | Daddona et al. | 156/73.1 |
| 6,103,033 A | 8/2000 | Say et al. | 205/777.5 |
| 6,120,676 A | 9/2000 | Heller et al. | 600/345 |
| 6,141,573 A | 10/2000 | Kurnik et al. | 600/309 |
| 6,142,939 A | 11/2000 | Eppstein et al. | 600/347 |
| 6,144,869 A | 11/2000 | Berner et al. | 600/345 |
| 6,175,752 B1 | 1/2001 | Say et al. | 205/777.5 |
| 6,207,400 B1 * | 3/2001 | Kwon | 435/14 |

FOREIGN PATENT DOCUMENTS

| | | |
|---|---|---|
| WO | WO 94/24263 | 10/1994 |
| WO | WO 96/00110 | 1/1996 |
| WO | WO 96/04947 | 2/1996 |
| WO | WO 96/12513 | 5/1996 |
| WO | WO 96/20022 | 7/1996 |
| WO | WO 97/09970 | 3/1997 |

* cited by examiner

*Primary Examiner*—Louise N. Leary
(74) *Attorney, Agent, or Firm*—Thomas P. McCracken

(57) ABSTRACT

Methods for sampling an analyte present in a biological system are provided. The methods entail use of particle delivery methods to obtain a sample of an analyte of interest from the system.

27 Claims, 3 Drawing Sheets

Glucose profile of Subject 1

Glucose profile of Subject 2

NON-OR MINIMALLY INVASIVE MONITORING METHODS USING PARTICLE DELIVERY METHODS

CROSS-REFERENCE TO RELATED APPLICATIONS

This application is a continuation of Ser. No. 09/390,068, filed Sep. 3, 1999, now U.S. Pat. No. 6,207,400, from which application priority is claimed pursuant to 35 U.S.C. § 120 and which application is incorporated herein by reference in its entirety. This application also is related to U.S. provisional application Ser. No. 60/099,157, filed Sep. 4, 1998, from which priority is claimed pursuant to 35 U.S.C. § 119(e)(1) and which application is incorporated herein by reference in its entirety.

TECHNICAL FIELD

This invention relates generally to methods of monitoring the presence and/or concentration of target analytes in an aqueous biological system. More particularly, the invention relates to methods for determining the presence, for example measuring the concentration, of one or more analytes in a transdermally extracted sample. One important application of the invention involves a sampling method for monitoring blood glucose using non-invasive or minimally invasive sampling techniques.

BACKGROUND

A number of tests are routinely performed on humans to evaluate the amount or existence of substances present in blood or other body fluids. These tests typically rely on physiological fluid samples removed from a subject, either using a syringe or by pricking the skin. One particular test entails self-monitoring of blood glucose levels by diabetics.

Diabetes is a major health concern, and treatment of the more severe form of the condition, Type I (insulin-dependent) diabetes, requires one or more insulin injections per day. Insulin controls utilization of glucose or sugar in the blood and prevents hyperglycemia which, if left uncorrected, can lead to ketosis. On the other hand, improper administration of insulin therapy can result in hypoglycemic episodes, which can cause coma and death. Hyperglycemia in diabetics has been correlated with several long-term effects, such as heart disease, atherosclerosis, blindness, stroke, hypertension and kidney failure.

The value of frequent monitoring of blood glucose as a means to avoid or at least minimize the complications of Type I diabetes is well established. According to the National Institutes of Health, glucose monitoring is recommended 4–6 times a day. Patients with Type II (non-insulin-dependent) diabetes can also benefit from blood glucose monitoring in the control of their condition by way of diet and exercise.

Conventional blood glucose monitoring methods generally require the drawing of a blood sample (e.g., by finger prick) for each test, and a determination of the glucose level using an instrument that reads glucose concentrations by electrochemical or colorimetric methods. Type I diabetics must obtain several finger prick blood glucose measurements each day in order to maintain tight glycemic control. However, the pain and inconvenience associated with this blood sampling, along with the fear of hypoglycemia, has lead to poor patient compliance, despite strong evidence that tight control dramatically reduces long-term diabetic complications. In fact, these considerations can often lead to an abatement of the monitoring process by the diabetic.

SUMMARY OF THE INVENTION

The present invention provides a method for sampling an analyte present in a biological system. More especially, the invention provides a method for sampling an analyte present beneath a target skin or mucosal surface of an individual, said method comprising:

(a) accelerating particles into and/or across said target surface, wherein acceleration of said particles into or across the target surface is effective to allow passage of a fluid sample from beneath the target surface to the target surface; and (b) determining the presence of said analyte in said fluid sample.

The invention also provides use of an inert material for the manufacture of a particulate composition for sampling an analyte present beneath a target skin or mucosal surface of an individual by such a method. The method can be used to determine, for example qualitatively or quantitatively, the presence of an analyte of interest in the biological system. The method can also be used to determine the amount or concentration of the analyte of interest. In addition, the method can be used to continually or continuously measure the concentration of the analyte.

The method entails accelerating particles into and/or across a target surface of the biological system such that the particles allow a quantity of an analyte (e.g., a fluid sample containing or suspected of containing an analyte of interest) to pass from beneath the target surface. The analyte can then be contacted with a sensing apparatus to derive a raw detectable signal therefrom, wherein the raw signal is either indicative of the presence of the analyte, or related to the analyte concentration. If desired, the analyte can be collected from the target surface prior to contact with the sensing apparatus.

Sampling is carried out such that the analyte of interest is transdermally extracted from the biological system. In this regard, the terms "transdermal extraction" and "transdermally extracted" intend any non-invasive, or at least minimally invasive method of using particle delivery techniques to facilitate extraction of an analyte from beneath a tissue surface, across skin or mucosal tissue for subsequent analysis on, or collection and analysis from the surface thereof. The terms further include any such extraction whether or not coupled with application of skin penetration enhancers, negative pressure (vacuum or suction), or other extraction technique.

Analyte (generally within a volume of fluid) which is extracted from the biological system is then either contacted directly with a sensing apparatus for obtaining a raw signal indicative of the presence and/or concentration of the analyte of interest, or collected and then contacted with the sensing apparatus. This raw signal can be obtained using any suitable sensing methodology including, for example, methods which rely on direct contact of a sensing apparatus with the biological system, methods which rely on contact with a collected amount of the extracted analyte, and the like. The sensing apparatus used with any of the above-noted methods can employ any suitable sensing element to provide the raw signal including, but not limited to, physical, chemical, biochemical (e.g., enzymatic, immunological, or the like), electrochemical, photochemical, spectrophotometric, polarimetric, calorimetric, radiometric, or like elements. In preferred embodiments of the invention, a biosensor is used which comprises an electrochemical sensing element.

The analyte can be any specific substance or component that one is desirous of detecting and/or measuring in a chemical, physical, enzymatic, or optical analysis. Such analytes include, but are not limited to, toxins, contaminants, amino acids, enzyme substrates or products indicating a disease state or condition, other markers of disease states or conditions, drugs of recreation and/or abuse, performance-enhancing agents, therapeutic and/or pharmacologic agents, electrolytes, physiological analytes of interest (e.g., calcium, potassium, sodium, chloride, bicarbonate ($CO_2$), glucose, urea (blood urea nitrogen), lactate, and hemoglobin), lipids, and the like. In preferred embodiments, the analyte is a physiological analyte of interest, for example glucose, or a chemical that has a physiological action, for example a drug or pharmacological agent. As will be understood by the ordinarily skilled artisan upon reading the present specification, there are a large number of analytes that can be sampled using the present methods.

Accordingly, it is a primary object of the invention to provide a method for sampling an analyte present in a biological system. The analyte is typically present beneath a target skin or mucosal surface of an individual. The method entails the steps of accelerating sampling particles into and/or across a target surface. Acceleration of the sampling particles into or across the target surface is effective to allow passage of a quantity of the analyte (typically a fluid sample comprising the analyte) from beneath the target surface to the target surface. The sample can contain a diagnostic quantity of the analyte. The presence and/or amount or concentration of the analyte which is so extracted is then determined by direct contact with a sensing apparatus, or the analyte is collected from the target surface and then contacted with a sensing apparatus.

An advantage of the invention is that the sampling process can be readily practiced inside and outside of the clinical setting and without pain.

These and other objects, aspects, embodiments and advantages of the present invention will readily occur to those of ordinary skill in the art in view of the disclosure herein.

DETAILED DESCRIPTION OF THE PREFERRED EMBODIMENTS

Figure 1:
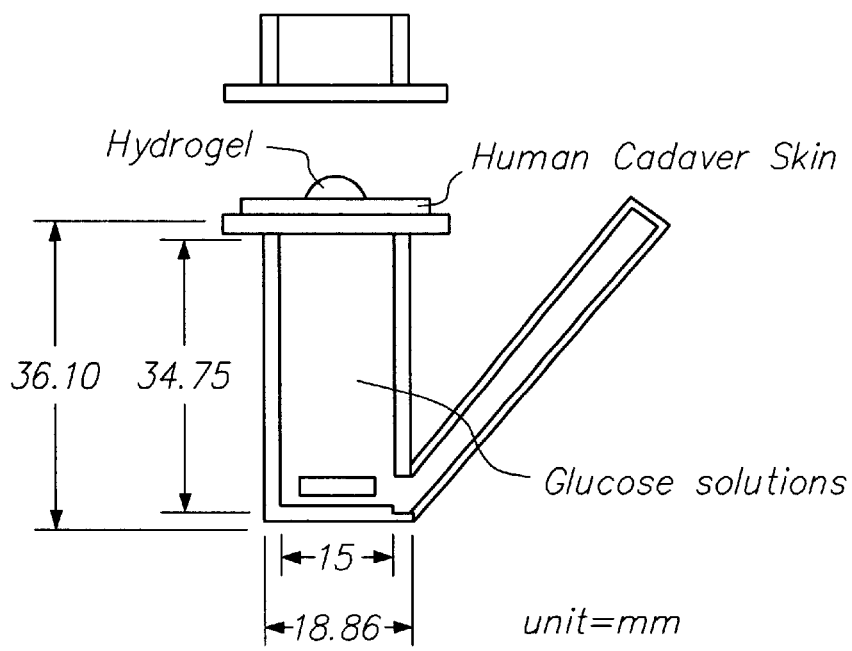
FIG. 1 is a schematic diagram of the modified Franz cell used in Example 1 for in vitro glucose measurement.

Before describing the present invention in detail, it is to be understood that this invention is not limited to particularly exemplified analytes or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a," "an" and "the" include plural referents unless the content clearly dictates otherwise. Thus, for example, reference to "a particle" includes a mixture of two or more such particles, reference to "an analyte" includes mixtures of two or more such analytes, and the like.

A. Definitions

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed, and are intended to be defined as indicated below.

The term "analyte" is used herein in its broadest sense to denote any specific substance or component that is being detected and/or measured in a physical, chemical, biochemical, electrochemical, photochemical, spectrophotometric, polarimetric, calorimetric, or radiometric analysis. A detectable signal can be obtained, either directly or indirectly, from such a material. In preferred embodiments, the analyte is a physiological analyte of interest (e.g., a physiologically active material), for example glucose, or a chemical that has a physiological action, for example a drug or pharmacological agent.

As used herein, the term "pharmacological agent" intends any compound or composition of matter which, when administered to an organism (human or animal), induces a desired pharmacologic and/or physiologic effect by local and/or systemic action.

As used herein, the term "sampling" means extraction of a substance from any biological system across a membrane, generally across skin or tissue. The membrane can be natural or artificial, and is generally animal in nature, such as natural or artificial skin, blood vessel tissue, intestinal tissue, and the like. A "biological system" thus includes both living and artificially maintained systems.

The term "collection reservoir" is used to describe any suitable containment means for containing a sample extracted from an individual using the methods of the present invention. Suitable collection reservoirs include, but are not limited to, pads, membranes, dipsticks, swabs, tubes, vials, cuvettes, capillary collection devices, and miniaturized etched, ablated or molded flow paths.

The terms "sensing device" or "sensing apparatus" encompass any device that can be used to measure the concentration of an analyte of interest. Preferred sensing devices for detecting blood analytes generally include electrochemical devices and chemical devices. Examples of electrochemical devices include the Clark electrode system (see, e.g., Updike et al. (1967) *Nature* 214:986–988), and other amperometric, coulometric, or potentiometric electrochemical devices. Examples of chemical devices include conventional enzyme-based reactions as used in the Lifescan® glucose monitor (see, e.g., U.S. Pat. No. 4,935,346 to Phillips et al.). Detection and/or quantitization of a chemical signal can also be carried out using readily available spectrophotometric monitoring devices.

The term "individual" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

B. General Methods

The invention relates to a method for sampling analytes present in a biological system, typically a physiologically active material that is present beneath a target skin or mucosal surface of an individual. The method entails two general steps, a sampling step and a determination step. The sampling step can be generalized as follows. Small sampling particles are accelerated into and/or across a target surface. Acceleration and penetration of these particles is sufficient to create passages which allow a quantity of an analyte of interest to flow, exude or otherwise pass from beneath the target surface to the target surface. The target surface generally has an overall size ranging from about 0.1 to about 5 $cm^2$.

The sampling particles typically comprise an inert material. The material may be dissolvable such as commonly employed physiologically acceptable soluble materials including sugars (e.g., mannitol, sucrose, lactose, trehalose, and the like) and soluble or dissolvable polymers. Alternatively, the sampling particles can be comprised of insoluble materials such as starch, $TiO_2$, calcium carbonate, phosphate salts, hydroxy apatite, or even polymers or metals such as gold, platinum or tungsten. Insoluble materials are sloughed off with the normal skin or mucosal tissue renewal process. Preferred materials are lactose, lactic acid, mannitol and polyethylene glycol such as PEG 8000.

If desired, the sampling particles can be coated with a locally active agent which facilitates the sampling step. For example, the sampling particles can be coated with a pharmacological agent such as a vasoactive agent or an anti-inflammatory agent. The vasoactive agent is generally used to provide short-acting vasoactivity in order to maximize fluid access (maximize the analyte sample), whereas the anti-inflammatory agent is generally used to provide local anti-inflammatory action to protect the target site. The sampling particles can also be coated with an osmotically active agent to facilitate the sampling process.

The sampling particles can be delivered from a needleless syringe system such as those described in commonly owned International Publication Nos. WO 94/24263, WO 96/04947, WO 96/12513, and WO 96/20022, all of which are incorporated herein by reference. Delivery of sampling particles from these needleless syringe systems is generally practiced with particles having an approximate size generally ranging from 0.1 to 250 $\mu$m, preferably ranging from about 10–70 $\mu$m. Particles larger than about 250 $\mu$m can also be delivered from the devices, with the upper limitation being the point at which the size of the particles would cause untoward pain and/or damage to the tissue.

The actual distance which the delivered particles will penetrate a target surface depends upon particle size (e.g., the nominal particle diameter assuming a roughly spherical particle geometry), particle density, the initial velocity at which the particle impacts the surface, and the density and kinematic viscosity of the targeted skin tissue. In this regard, optimal particle densities for use in needleless injection generally range between about 0.1 and 25 $g/cm^3$, preferably between about 0.9 and 1.5 $g/cm^3$, and injection velocities generally range between about 100 and 3,000 m/sec. With appropriate gas pressure, particles having an average diameter of 10–70 $\mu$m can be readily accelerated through the nozzle at velocities approaching the supersonic speeds of a driving gas flow. Preferably, the pressure used when accelerating the particles will be less than 30 bar, preferably less than 25 bar and most preferably 20 bar or less.

Alternatively, the sampling particles can be delivered from a particle-mediated delivery device such as a so-called "gene-gun" type device which delivers particles using either a gaseous or electric discharge. An example of a gaseous discharge device is described in U.S. Pat. No. 5,204,253. An explosive-type device is described in U.S. Pat. No. 4,945,050. One example of a helium discharge-type particle acceleration apparatus is the PowderJect XR® instrument (PowderJect Vaccines, Inc., Madison), Wis., which instrument is described in U.S. Pat. No. 5,120,657. An electric discharge apparatus suitable for use herein is described in U.S. Pat. No. 5,149,655. The disclosure of all of these patents is incorporated herein by reference.

After the sampling particles have been delivered into the target surface, a fluid sample passes to the target surface. Typically this is a sample of, or containing, interstitial fluid. Passage of the fluid sample to the surface may be substantially instantaneous, or may occur over a period of time. The quantity of the sample which is released to the target surface may be varied by altering conditions such as the size and/or density of sampling particles and the settings of the apparatus used to delivery the particles. The quantity of fluid released may often be small, such as <1 $\mu$l which is generally sufficient for detection of the analyte.

Once the sample has passed to the target surface, the presence and/or amount or concentration of the analyte in the sample is determined. The sample may be contacted with a suitable sensing apparatus. This detection step can, of course, be carried out in a continual or continuous manner. Continual or continuous detection allows for monitoring of target analyte concentration fluctuations. Furthermore, the sample believed to contain the analyte can first be collected from the target surface prior to being contacted with the sensing apparatus.

The sample may be collected from the target surface in a number of ways. For example pads, membrane dipsticks, swabs, tubes, vials, curvettes, capilliary collection devices and miniaturized etched, ablated or molded flow paths may be used as collection reservoirs. In a preferred aspect an absorbent material is passed over the target surface to absorb the fluid sample from the target surface for subsequent detection of the presence or amount of analyte. The absorbent material may be in the form of a pad or swab. The absorbent material may additionally incorporate means to facilitate detection of the analyte such as an enzyme as described in more detail below.

The absorbent material may be applied to the target surface and subsequently contacted with a detection means to detect the analyte. The absorbent material may comprise a hydrogel. Suitable gelling agents for forming a hydrogel include carbopol, calcium lactate, cellulose gum, klucel (HPMC), natrosol, gelatin powder or sodium alginate. The gelling agents may be present in water at levels such as 1% by weight in water.

The gel may be applied to the target surface and sufficient time allowed for analyte from the target surface to equilibrate in the gel prior to the detection step. The time may be quite short such as from 30 seconds to 5 minutes. Detection may then be carried out by applying the sensing means to the gel such as by contacting a membrane containing a suitable enzyme system for the analyte with the hydrogel.

The determination step can be generalized as follows. An initial step can entail obtaining a raw signal from a sensing device, which signal is related to a target analyte present in the biological system. The raw signal can then be used directly to obtain an answer about the analyte, for example a yes or no answer relating to the presence of the analyte, or a direct measurement indicative of the amount or concentration of the extracted analyte. The raw signal can also be used indirectly to obtain information about the analyte. For example, the raw signal can be subjected to signal processing steps in order to correlate a measurement of the sampled analyte with the concentration of that analyte in the biological system. Such correlation methodologies are well known to those skilled in the art.

Detection may be carried out by any suitable method which allows for detection of a derived analyte. The analysis may be physical, chemical, biochemical, electrochemical, photochemical, spectrophotometric, polermetric, colormetric or radiometric analysis.

In order to facilitate detection of the analyte, an enzyme may be disposed on the active surface or portion of a sensing apparatus which is contacted with the extracted analyte (e.g., an extracted sample containing the analyte), or included within one or more collection reservoirs which are used to collect the extracted analyte. Such enzymes must be capable of catalyzing a specific reaction with the extracted analyte (e.g., glucose) to the extent that a product of the reaction can be sensed (e.g., detected electrochemically from the generation of a current which current is detectable and proportional to the amount of the analyte which is reacted). A suitable enzyme is glucose oxidase which oxidizes glucose to gluconic acid and hydrogen peroxide. The subsequent detection of hydrogen peroxide on an appropriate biosensor electrode generates two electrons per hydrogen peroxide molecule which create a current which can be detected and related to the amount of glucose entering the device. Glucose oxidase (GOx) is readily available commercially and has well known catalytic characteristics. However, other enzymes can also be used, so long as they specifically catalyze a reaction with an analyte or substance of interest to generate a detectable product in proportion to the amount of analyte so reacted.

A number of other analyte-specific enzyme systems can be used in the methods of the invention. For example, when using a common biosensor electrode that detects hydrogen peroxide, suitable enzyme systems can be used to detect ethanol (an alcohol oxidase enzyme system), or similarly uric acid (a urate oxidase system), cholesterol (a cholesterol oxidase system), and theophylline (a xanthine oxidase system). Hydrogels containing these analyte-specific enzyme systems can be prepared using readily available techniques familiar to the ordinarily skilled artisan.

Preferred sensing devices are patches that include an enzyme or other specific reagent which reacts with the extracted analyte of interest to produce a detectable color change or other chemical signal. The color change can be assessed by comparison against a standard to determine analyte amount, or the color change can be detected using standard electronic reflectance measurement instruments. One such system is transdermal glucose monitoring system available from Technical Chemicals and Products, Inc (TCPI) of Pompano Beach, Fla. Another suitable system is described in U.S. Pat. No. 5,267,152 to Yang et al. (a device and method for measuring blood glucose concentration using near-IR radiation diffuse-reflection laser spectroscopy. Similar near-IR spectrometric devices are also described in U.S. Pat. No. 5,086,229 to Rosenthal et al. and U.S. Pat. No. 4,975,581 to Robinson et al. U.S. Pat. No. 5,139,023 to Stanley describes a blood glucose monitoring apparatus that relies on a permeability enhancer (e.g., a bile salt) to facilitate transdermal movement of glucose along a concentration gradient established between interstitial fluid and a receiving medium. U.S. Pat. No. 5,036,861 to Sembrowich describes a passive glucose monitor that collects perspiration through a skin patch, where a cholinergic agent is used to stimulate perspiration secretion from the eccrine sweat gland. Similar perspiration collection devices are described in U.S. Pat. No. 5,076,273 to Schoendorfer and U.S. Pat. No. 5,140,985 to Schroeder. Detection of extracted glucose is carried out using standard chemical (e.g., enzymatic) colormetric or spectrometric techniques.

Alternatively, an iontophoretic transdermal sampling system can be used in conjunction with the present invention, for example where the instant particle method is used to pre-treat a skin site to facilitate improved sampling from a GlucoWatch system (Cygnus, Redwood, Calif.). This iontophoretic system is described in Gliebfeld et al (1989), Pharm. Res. 6(11): 988 et seq and U.S. Pat. No. 5,771,890.

C. Experimental

Below are examples of specific embodiments for carrying out the methods of the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Introduction

The interstitial fluid is the clear body fluid between cells on the top surface layer of skin. The glucose level in this fluid directly indicates the glucose level in blood. A needleless syringe device can create diffusion pathway into these layers and will allow the collection of a small amount (<1 ml) of interstitial fluid from which the glucose level can be measured.

Materials and Methods

Lactose monohydrate, NF, grade, was obtained from Amresco® (Solon, Ohio). The lactose powder was sieved to 38–53 $\mu$m using U.S. Standard Sieve (Chicago, Ill.). D-(+) glucose was obtained from Sigma (St. Louis, Mo.). Human cadaver skin was supplied from New York Firefighter Skin Bank (New York, N.Y.), was pretreated with 80% balanced salt solution, 10% calf serum and 10% glycerol and frozen at the skin bank. The skin was used as supplied after 1–2 hours thawing at room temperature.

Modified Franz cells (6.9 ml) were designed for investigation of in vitro glucose extraction (FIG. 1). The donor part in the bottom of the cell was filled with different glucose concentrations ranging from 10–500 mg/dl. The temperature of the glucose solution was maintained at 32° C. during the experiments. Human cadaver skin of a thickness of 200–300 mm was used. The skin was punched out using a 1 inch (2.54 cm) die cutter and placed on the modified Franz cell.

After a few hours for equilibration, 2 mg of lactose particles of 38–53 $\mu$m were filled into tri-laminate cassette of 20 $\mu$m polycarbonate membrane and were injected onto the skin tissue using a PowderJect ND 1 needleless syringe device fitted with a supersonic nozzle. Device pressure for particle administration was 20 bar. Then, 5 $\mu$l of hydrogel was placed on the top of the injected skin and a One Touch enzymatic membrane (Lifescan, Milpitas, Calif.) was contacted with the gel for one minute. The optical density of the membrane was then measured with a Densitometer (Hercules, Calif.).

Results

Figure 2:
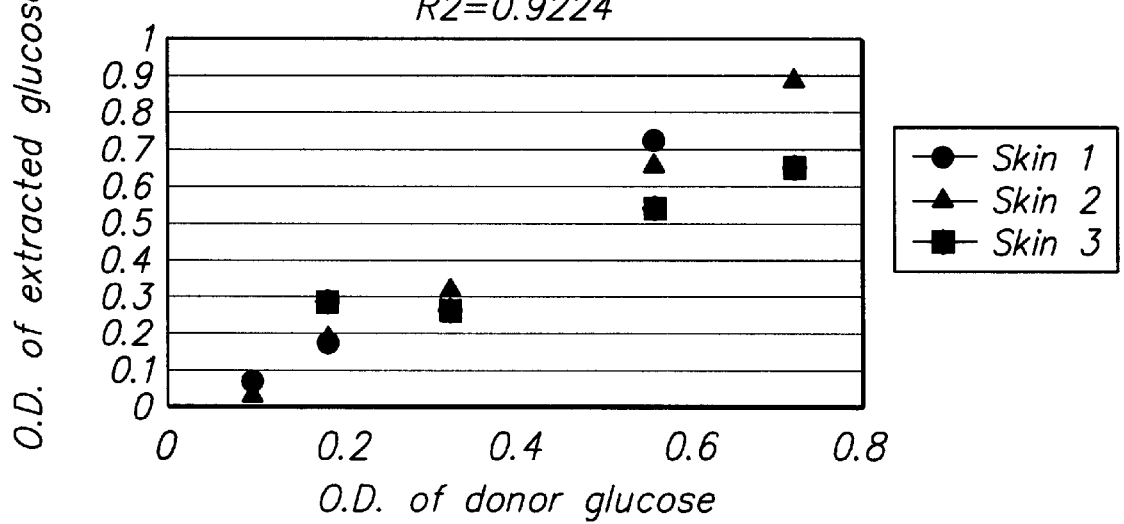
FIG. 2 is a plot of optical density of glucose solution in donor compartment and glucose extracted from three different skins in the in vitro study of Example 1.

Table 1 is a summary of measured optical density of membranes contacted with the donor part (bottom part of the Franz cell) or the hydrogel at the top of the treated skin. As can be seen, the optical density of extracted glucose from the top of the three different skin samples is proportionally increased from 0.04–0.08 to 0.65–0.89 as the optical density of donor part is increased from 0.10 to 0.71. FIG. 2 is the summary plot of optical density from three skin samples over donor part. The correlation ($r^2$ value) was calculated to be 0.92 over the three skin samples.

These in vitro experimental results demonstrate that there is good correlation ($r^2$=0.92) between the measured values of extracted glucose using the particle delivery methods of the present invention and donor compartment which simulated human interstitial fluid.

TABLE 1

Glucose standard solution and optical density of glucose solution in donor compartment and glucose extracted from three different skin samples

| Glucose Standard (mg/dl) | Donor Compartment | Skin 1 | Skin 2 | Skin 3 |
|---|---|---|---|---|
| 10 | 0.099 | 0.06 | 0.04 | 0.075 |
| 50 | 0.184 | 0.17 | 0.19 | 0.285 |
| 100 | 0.323 | 0.265 | 0.325 | 0.26 |
| 250 | 0.56 | 0.725 | 0.665 | 0.54 |
| 500 | 0.721 | — | 0.895 | 0.65 |

EXAMPLE 2

Introduction

The in vitro study with human cadaver skin set out in Example 1 demonstrated that there is a solid correlation of "systemic" glucose levels with fluid samples accessed via a particle delivery method ($r^2$=0.92). Therefore, this study was carried out to compare glucose levels from two blood sources (venous blood glucose and capillary blood glucose) with the glucose level of interstitial fluid accessed via a needleless injection device in human subjects.

Additionally, on the needleless injection sites, visual grade of erythema or edema using the Draize scale, change in chromaticity, change in transepidermal water loss (TEWL) and any sensation of pain (VAS) were measured to indicate stratum corneum disruption and confirm particle penetration. Measurements were performed immediately after particle injection and at 24 and 48 hours post-sampling. These measurements profile any correlation between venous glucose, capillary glucose and interstitial glucose with skin tolerability.

Materials and Methods 120 diabetic subjects were included in the study. The subjects were male or female Type I or Type II diabetics of ages 18–70 but excluding diabetics with any skin disorder at the sites of testing, including eczema, psoriasis, etc. or with a history of recurrent skin infections. Sampling sites were antecubital fossa (venous), fingertip (capillary) and volar forearm (particle delivery).

The needleless syringe particle delivery device and compounds were as follows:

Powder: lactose, particle size of 20–38 mm, sieved.
Cassette: trilaminate with 10 μm polycarbonate membranes (upstream membrane was slit), 1.0 mg powder payload, prepared and packaged in a clean laboratory environment and terminally sterilised with γ radiation.
Device: A dermal PowderJect™ ND1 needleless syringe device fitted with a supersonic nozzle, 5 cc expansion chamber modified to accommodate trilaminate cassettes, 10 bar compressed air pressure, push button stainless gas cylinder.

The needleless syringe device was held as vertically as possible with the nozzle placed firmly against the skin, ensuring there was no gap between the skin and the end of the device. The device was actuated by pressing down the button at the top.

TEWL and chromaticity were assessed for each volar forearm injection site prior to powder delivery. After the powder was delivered to the site, TEWL was measured for each injection site. Each subject was asked to describe the sensation of administration in a few words and record the sensation on a 100 mm visual analog scale (VAS) for pain, with 100 being the pain of finger-stick and 0 being no pain.

A LifeScan™ glucose detection membrane strip was moistened with 5 μl of hydrogel and applied to the powder-injected site for 1 minute. The treated sites were swabbed and chromaticity measured for comparison with pre-treatment values. Capillary blood samples were collected by finger stick for glucose analysis using the LifeScan One-Touch system. Blood samples were collected from a vein in the antecubital fossa for glucose analysis. The colour intensity of the membranes were quantified with the Bio-Rad densitometer. TEWL and chromaticity of the injected site were measured at 24 and 48 hours post injection.

The protocol used for an oral glucose tolerance test was as follows. All drug therapy that could affect the test was discontinued for at least 3 days before the test. The subjects were instructed to ingest a carbohydrate intake of at least 150 g/day for 3 days before the test, and fast 14 to 15 hours (from 6 pm of the day preceding the test to 8 to 9 am of the day of the test). Test subjects abstained from tobacco, coffee, tea, food, and alcohol during the test. The subjects sat quietly upright during the test. Slow walking was permitted but vigorous exercise was avoided. Before a glucose load was given, Fasting Plasma Glucose (FPG) was measured via the venous, capillary and interstitial glucose sampling techniques described above. 75 g of glucose was given as a 25% solution (400 ml). Samples were collected and the capillary and interstitial glucose levels were measured as above at 30, 60, 90, 120 min.

Results

Figure 3:
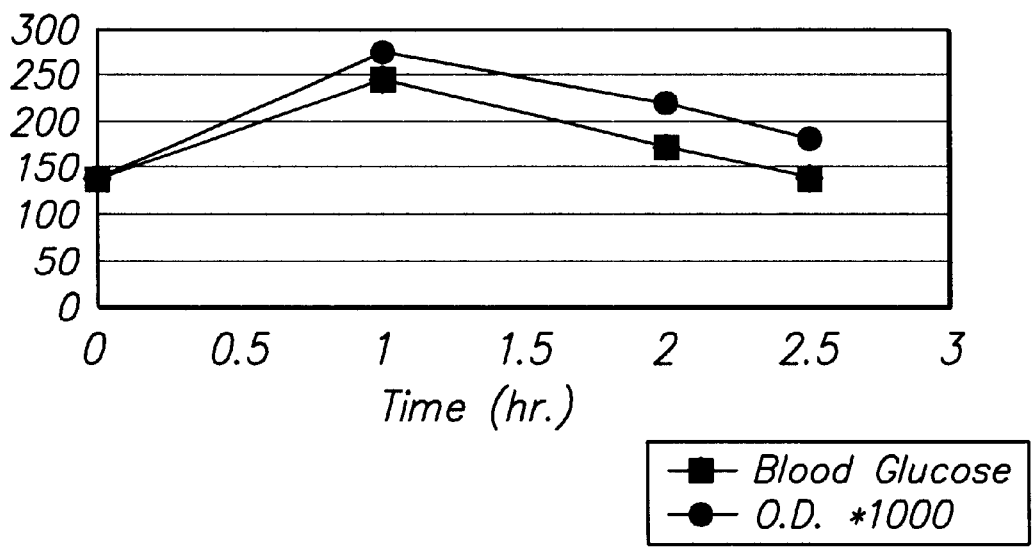
FIGS. 3 to 5 are glucose tolerance test profiles on three individual subjects from the in vivo study of Example 2.
Figure 4:
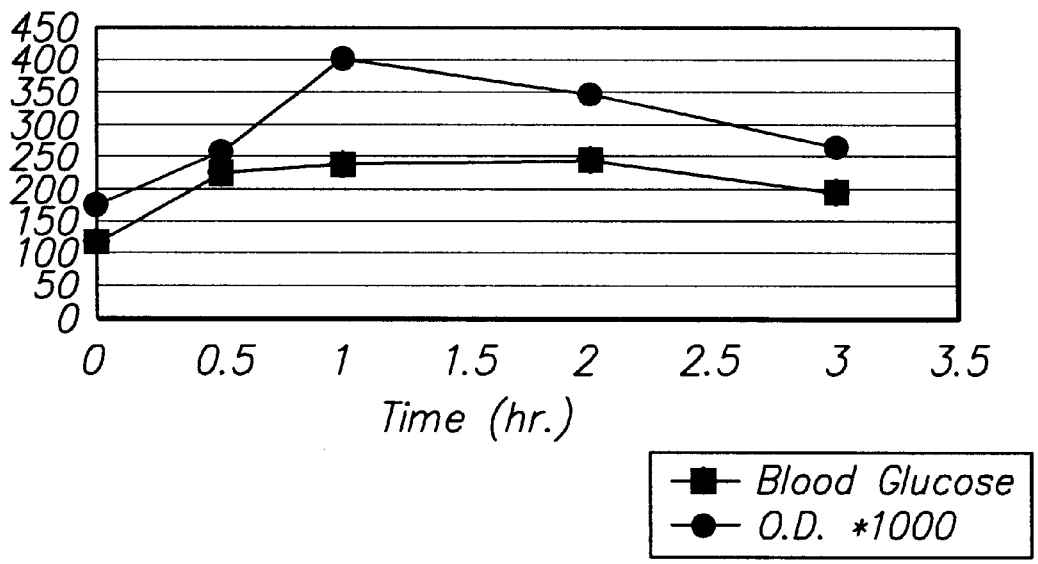
Figure 5:
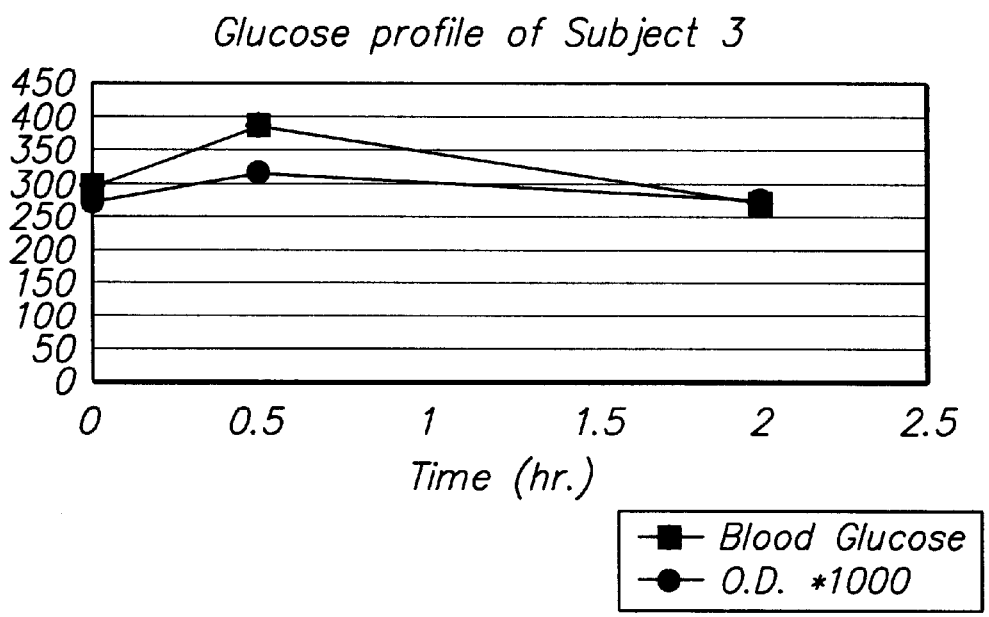

The glucose tolerance test results from three subjects are depicted in FIG. 3 to FIG. 5. The blood glucose concentration (mg/dl) and optical density from reaction with glucose in interstitial fluid are shown. In order to combine the results into the same Figure, optical density was multiplied by 1000.

The dynamic glucose range of subject 1 was 150 to 270 mg/dl. The optical density according to the blood glucose value correlated well with venous glucose concentration (FIG. 3). The dynamic glucose range of subject 2 was 160 mg/dl to 400 mg/dl. There was a correlation between venous glucose and optical density except at the one hour time point (FIG. 4). A similar trend could be observed in subject 3 (FIG. 5).

Figure 6:
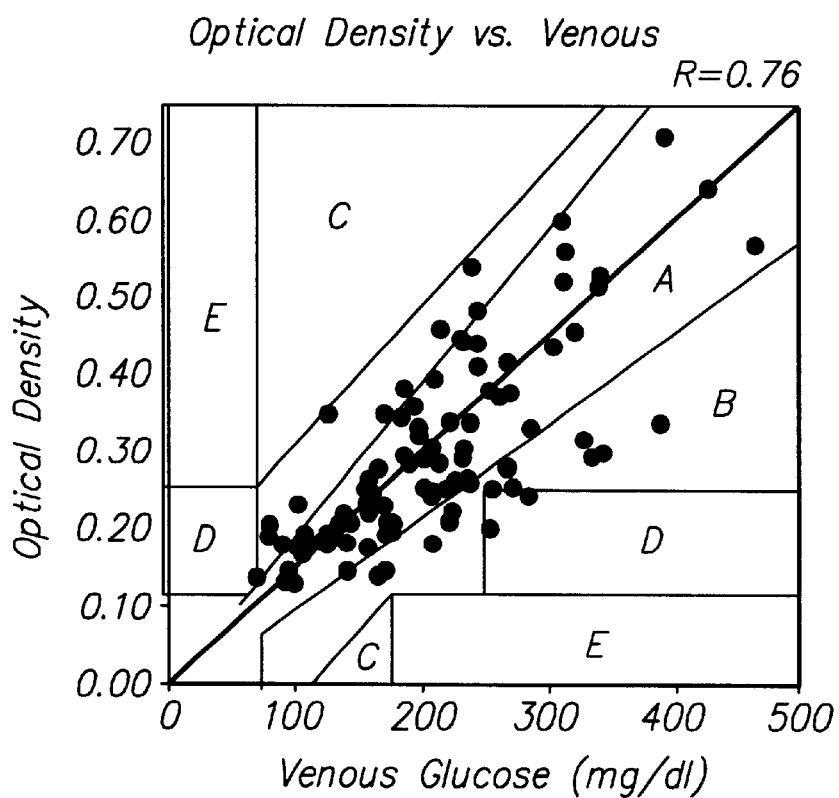
FIG. 6 is a plot of optical density over venous glucose value from the study of Example 2.

In FIG. 6, the optical density readings from interstitial fluid glucose were plotted over venous blood glucose of all subjects. The error grid method was applied to the collected data and plotted. Most data points are located in region A and B which are clinically correlated regions. The r value from a linear regression analysis was 0.76. Table 2 reports a comparison of error grid analyses between the invasive Glucometer, the iontophoretic GlucoWatch method, and the particle delivery method according to the invention.

TABLE 2

Clinical result comparision between Glucometer ®,
Gluco Watch ® and the invention

| Zone | Glucometer ® | Gluco Watch ® | Invention |
|------|--------------|---------------|-----------|
| A    | 91.3         | 73.9          | 77.3      |
| B    | 7.9          | 22.7          | 20.8      |
| C    | 0            | 0.06          | 0         |
| D    | 0.8          | 3.41          | 1.9       |
| E    | 0            | 0             | 0         |

With respect to pain, most subjects (>90%) preferred the particle delivery method according to the invention over the Glucometer and GlucoWatch glucose measuring methods. However, there was some erythema noted in some subjects that resolved after 3–4 days with the methodology of the invention.

Accordingly, novel monitoring methods are disclosed. Although preferred embodiments of the subject invention have been described in some detail, it is understood that obvious variations can be made without departing from the spirit and the scope of the invention as defined by the appended claims.

What is claimed is:

1. A measured quantity of a powder composition comprising sampling particles, said powder composition comprising size-selected particles of an inert material selected from the group consisting of sugars, soluble or dissolvable polymers, starch, $TiO_2$, calcium carbonate, phosphate salts, lactic acid and hydroxy apatite.

2. The powder composition of claim 1 wherein the size-selected particles have a size ranging from 0.1 to 250 $\mu$m.

3. The powder composition of claim 1 wherein the size-selected particles have a size ranging from 10 to 70 $\mu$m.

4. The powder composition of claim 1 wherein the size-selected particles have a size ranging from 28–53 $\mu$m.

5. The powder composition of claim 1 wherein the inert material is a sugar.

6. The powder composition of claim 5, wherein the sugar is selected from the group consisting of mannitol, sucrose, lactose and trehalose.

7. The powder composition of claim 6 wherein the sugar is lactose.

8. A cassette containing the powder composition of claim 1.

9. A needleless syringe containing the powder composition of claim 1.

10. A particle-mediated delivery device containing the powder composition of claim 1.

11. Sampling particles, comprising particles of an inert material coated with a locally active agent.

12. The sampling particles of claim 11 wherein the agent is a vasoactive agent or an anti-inflammatory agent.

13. The sampling particles of claim 11 wherein the agent is an osmotically active agent.

14. The sampling particles of claim 11 wherein the particles have a size ranging from 0.1–250 $\mu$m.

15. The sampling particles of claim 14 wherein the particles have a size ranging from 10–70 $\mu$m.

16. A needleless syringe containing the sampling particles of claim 11.

17. A particle-mediated delivery device containing the sampling particles of claim 11.

18. A method for sampling an analyte present beneath a target skin or mucosal surface of an individual, said method comprising:

(a) creating passages in the target surface sufficient to allow said analyte to flow, exude or otherwise pass from beneath the target surface to the target surface; and (b) contacting the target surface with a sensing apparatus that detects the presence or amount of said analyte.

19. The method of claim 18 wherein the sensing apparatus is a patch.

20. The method of claim 18 wherein an absorbent material is applied to the target surface during step (b).

21. The method of claim 20 wherein the absorbent material is a hydrogel.

22. The method of claim 20 wherein the absorbent material is applied to the target surface for a time sufficient to allow analyte to equilibrate in the gel prior to detection of the presence or amount of the said analyte.

23. The method of claim 18 wherein the fluid sample passes from beneath the target surface over a period of time.

24. The method of claim 18 wherein step (a) comprises accelerating particles into and/or across said target surface to create said passages and step (b) further comprises collecting a sample from the target surface.

25. The method of claim 24 wherein the sample is collected into a collection means that is contacted with the target surface.

26. The method of claim 25 wherein the sample is collected using an ablated flow path.

27. The method of claim 18 wherein step (b) comprises collecting a sample from the target surface using a collection reservoir comprising a miniaturized etched, ablated or molded flow path.

\* \* \* \* \*